United States Patent [19]
Peyman

[11] Patent Number: 5,964,776
[45] Date of Patent: Oct. 12, 1999

[54] INTERNAL KERATOME APPARATUS AND METHOD FOR USING THE SAME TO FORM A POCKET/FLAP BETWEEN LAYERS OF A LIVE CORNEA

[76] Inventor: Gholam A. Peyman, 8654 Pontchartrain Blvd., Unit 1, New Orleans, La. 70124

[21] Appl. No.: 08/936,509

[22] Filed: Sep. 24, 1997

[51] Int. Cl.⁶ .................................................. A61B 17/32
[52] U.S. Cl. ........................ 606/166; 606/169; 606/172
[58] Field of Search .................................... 606/166, 169, 606/172

[56] References Cited

U.S. PATENT DOCUMENTS

| | | |
|---|---|---|
| 3,074,407 | 1/1963 | Moon et al. . |
| 4,298,004 | 11/1981 | Schachar et al. . |
| 4,648,400 | 3/1987 | Schneider et al. . |
| 4,662,370 | 5/1987 | Hoffmann et al. .................. 606/166 |
| 4,676,790 | 6/1987 | Kern . |
| 4,718,418 | 1/1988 | L'Esperance, Jr. . |
| 4,796,623 | 1/1989 | Krasner et al. .................. 606/166 |
| 4,840,175 | 6/1989 | Peyman . |
| 4,903,695 | 2/1990 | Warner et al. . |
| 5,063,942 | 11/1991 | Kilmer et al. . |
| 5,092,874 | 3/1992 | Rogers . |
| 5,203,865 | 4/1993 | Siepser .................................. 606/166 |
| 5,215,104 | 6/1993 | Steinert . |
| 5,290,301 | 3/1994 | Lieberman . |
| 5,318,044 | 6/1994 | Kilmer et al. . |
| 5,318,046 | 6/1994 | Rozakis . |
| 5,368,604 | 11/1994 | Kilmer et al. . |
| 5,403,335 | 4/1995 | Loomas et al. . |
| 5,496,339 | 3/1996 | Koepnick ........................ 606/166 X |
| 5,507,741 | 4/1996 | L'Esperance, Jr. . |
| 5,507,759 | 4/1996 | Nordan . |
| 5,843,105 | 12/1998 | Mathis et al. ....................... 606/166 |

FOREIGN PATENT DOCUMENTS

| | | |
|---|---|---|
| 3433581 | 3/1986 | Germany . |
| 448013 | 10/1974 | U.S.S.R. ............................ 606/166 |
| 1660698 | 4/1989 | U.S.S.R. . |
| 2242835 | 10/1991 | United Kingdom . |
| 93/20763 | 10/1993 | WIPO ................................ 606/166 |

OTHER PUBLICATIONS

Gerge J. Pardos, M.D., "Attention to detail is crucial in performing LASIK", 1995, Oscular Surgery News pp. 38–41.

Primary Examiner—Michael H. Thaler
Attorney, Agent, or Firm—Roylance,Abrams,Berdo & Goodman, L.L.P.

[57] ABSTRACT

An apparatus and method for forming a circularly or substantially circularly shaped pocket between layers of a live cornea, and then, expanding the pocket to form a flap-like layer at the front of the live cornea which is pivotally attached to the remainder of the cornea by a flap connecting section. The cutting tool of the apparatus preferably has a circular or substantially circular cutting portion which is inserted into the cornea and reciprocated to form the pocket. Suction is applied to the front surface of the cornea to stabilize the cornea during the pocket forming process.

27 Claims, 10 Drawing Sheets

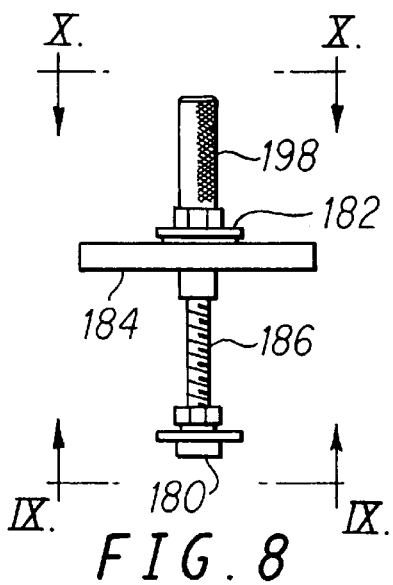
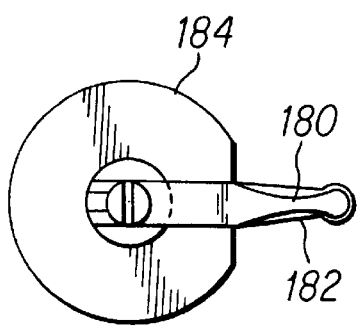
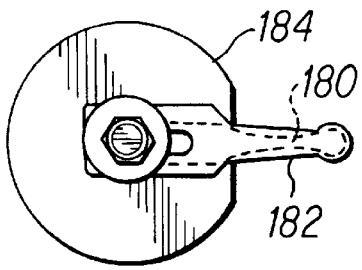
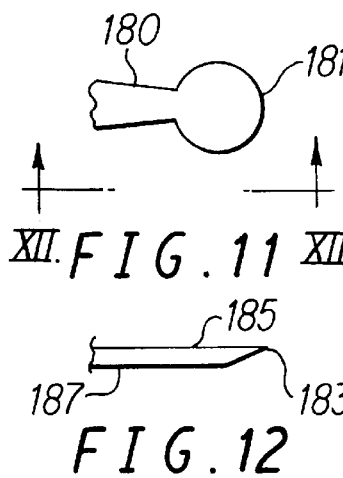
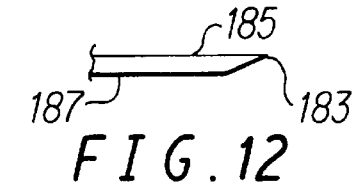
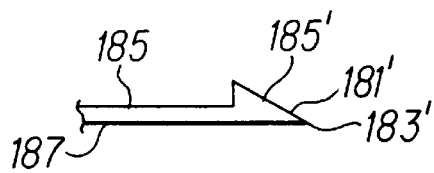
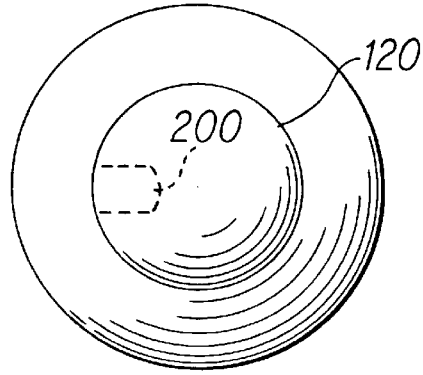
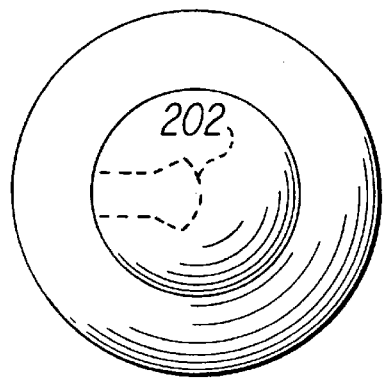

INTERNAL KERATOME APPARATUS AND METHOD FOR USING THE SAME TO FORM A POCKET/FLAP BETWEEN LAYERS OF A LIVE CORNEA

BACKGROUND OF THE INVENTION

1. Field of the Invention

The present invention relates to an internal keratome apparatus and method of using the same to form a pocket between layers of a live cornea More particularly, the present invention relates to an internal keratome apparatus having a circularly-shaped reciprocating blade, and a method for using the same to form a circularly-shaped pocket between layers of a live cornea, and then expanding the pocket to form a flap-like layer at the front surface of the live cornea.

2. Description of the Related Art:

A normal ametropic eye includes a cornea, lens and retina. The cornea and lens of a normal eye cooperatively focus light entering the eye from a far point, i.e., infinity, onto the retina. However, an eye can have a disorder known as ametropia, which is the inability of the lens and cornea to focus the far point correctly on the retina. Typical types of ametropia are myopia, hypermetropia or hyperopia, and astigmatism.

A myopic eye has either an axial length that is longer than that of a normal ametropic eye, or a cornea or lens having a refractive power stronger than that of the cornea and lens of an ametropic eye. This stronger refractive power causes the far point to be projected in front of the retina.

Conversely, a hypermetropic or hyperopic eye has an axial lens shorter than that of a normal ametropic eye, or a lens or cornea having a refractive power less than that of a lens and cornea of an ametropic eye. This lesser refractive power causes the far point to be focused on the back of the retina.

An eye suffering from astigmatism has a defect in the lens or shape of the cornea. Therefore, an astigmatic eye is incapable of sharply focusing images on the retina.

In order to compensate for the above deficiencies, a technique known as photorefractive keratectomy has been developed which involves the placement of lenses in front of the eye (for example, in the form of glasses or contact lenses). However, this technique is often ineffective in correcting severe vision disorders.

An alternative to photorefractive keratectomy is surgery. For example, in a technique known as myopic keratomileucis, a microkeratome is used to cut away a portion of the front of the live cornea from the main section of the live cornea. That cut portion of the cornea is then frozen and placed in a cyrolathe where it is cut and reshaped. Altering the shape of the cut portion of the cornea changes the refractive power of this cut portion, which thus effects the location at which light entering the cut portion of the cornea is focused. The reshaped cut portion of the cornea is then reattached to the main portion of the live cornea. Hence, this reshaped cornea will change the position at which the light entering the eye through the cut portion is focused, so that the light is focused more precisely on the retina, thus remedying the ametropic condition.

Keratophakia is another known surgical technique for correcting severe ametropic conditions of the eye by altering the shape of the eye's cornea In this technique, an artificial organic or synthetic lens is implanted inside the cornea to thereby alter the shape of the cornea and thus change its refractive power. Accordingly, as with the myopic keratomileucis technique, it is desirable that the shape of the cornea be altered to a degree which enables light entering the eye to be focused correctly on the retina.

Laser in situ keratomileusis (LASIK), as described, for example, in U.S. Pat. No. 4,840,175 to Peyman, the entire contents of which is incorporated herein by reference, is a further known surgical technique for correcting severe ametropic conditions of the eye by altering the shape of the eye's cornea. In the LASIK technique, a motorized blade is used to separate a thin layer of the front of the cornea from the remainder of the cornea in the form of a flap. The flap portion of cornea is lifted to expose an inner surface of the cornea. The exposed inner surface of the cornea is irradiated with laser light and thus reshaped by the laser light. The flap portion of the cornea is then repositioned over the reshaped portion and allowed to heal.

In all of these techniques, it is critical that the incisions are made in the cornea in a very precise manner. Otherwise, the vision may not be corrected properly, and worse, severe damage to the eye may occur.

Accordingly, it is necessary that the cornea be prevented from moving while the cutting or separating of the corneal layers is being performed. Also, it is necessary to flatten out the front portion of the cornea when the corneal layers are being separated or cut so that the separation or cut between the layers can be made at a uniform distance from the front surface of the cornea. Previous techniques for flatting out the front surface of the cornea involve applying pressure to the front surface of the cornea with an instrument such as a flat plate. However, these techniques can cause damage to the eye, in particular, the pressure can cause fluid to leak out of the eye.

In addition to stabilizing the cornea when the cutting or separating is being performed, the cutting tool must be accurately guided to the exact area at which the cornea is to be cut. Also, the cutting tool must be capable of separating layers of the cornea without damaging those layers or the surrounding layers.

Furthermore, when the keratophakia technique is being performed, it is desirable to separate the front layer from the live cornea so that the front layer becomes a flap-like layer that is pivotally attached to the remainder of the cornea and which can be pivoted to expose an interior layer of the live cornea on which the implant can be positioned. It is therefore necessary that the cutting tool be accurately guided to form a suitable flaplike layer without damaging the surface onto which the implant is to be positioned. It is also necessary that the angle of the cutting is controlled so that the surface of the exposed interior layer is at a desired angle (e.g., normal) with respect to the optical axis of the eye.

Additionally, because the epithelium cells which are present on the surface of the live cornea may become attached to the blade when the blade is being inserted into the live cornea and thus become lodged between the layers of the live cornea, thereby clouding the vision of the eye, it is desirable to remove the epithelium cells prior to performing the cutting.

Examples of known apparatuses for cutting incisions in the cornea are described in U.S. Pat. No. : 4,298,004 to Schachar et al., U.S. Pat. No. 5,215,104 to Steinert, and U.S. Pat. No. 4,903,695 to Warner, the entire contents of which are incorporated herein by reference.

However, a continuing need exists for an improved apparatus and method for cutting a precise incision into a live cornea. A continuing need also exists for an effective and simple method of removing the epithelium cells from the surface of the live cornea prior to inserting a cutting tool into the live cornea.

SUMMARY OF THE INVENTION

Accordingly, a primary object of the present invention is to provide an apparatus and method for precisely forming a substantially uniformly shaped pocket between layers of a live cornea, and then expanding the pocket to form a flap-like layer at the front of the live cornea which is pivotally attached to the remainder of the cornea by a flap connecting section.

This and other objects of the present invention are substantially achieved by an apparatus having a suction device that is adapted to be attached to the front surface of a live cornea to apply suction to the live cornea which prevents the live cornea from moving when the cutting is being performed. The apparatus includes a transparent or substantially transparent viewer through which the front surface of the cornea to which the suction is being applied can be viewed. The suction pulls the front surface of the cornea in a direction toward the viewer so that the front surface of the cornea contacts a bottom surface of the viewer and thus flattens out against that bottom surface. The cutting tool preferably has a circular or substantially circular blade which forms a circularly or substantially circularly shaped pocket between layers of the live cornea.

Specifically, the blade has a circular or substantially circularly-shaped portion at a location proximate to its cutting edge which first contacts the cornea when the blade is directed toward the cornea. The apparatus further includes a guide mechanism for guiding the blade in a direction toward the live cornea to which suction is being applied. The blade contacts the cornea so that the cutting edge is inserted into the cornea to separate adjacent layers of the cornea from each other. The blade is moved in a reciprocating manner in a direction transverse to the direction in which the blade is guided toward the cornea, to thus form a pocket between those adjacent layers of the live cornea.

Because the blade has the circular or substantially circular-shaped portion, the pocket formed between the adjacent layers of the cornea is circular or substantially circular in shape. The reciprocating movement of the blade is restricted to form the pocket. However, the reciprocating motion of the blade can be extended to enable the blade to expand the pocket to form a flap-like layer at the front surface of the cornea that is attached to the remainder of the cornea by an attaching portion.

Another object of the present invention is to provide an apparatus and method for effectively removing the epithelium cells from the surface of the live cornea prior to inserting the cutting tool into the live cornea. To achieve this object, the present invention provides an instrument for applying an alcohol mixture to the surface of the live cornea prior to inserting the cutting tool into the live cornea. The amount of time that the alcohol mixture will be applied to the surface of the live cornea is proportionate to the concentration of alcohol in the mixture.

These and other objects and advantages of the invention will become more apparent and more readily appreciated from the following detailed description of the presently preferred exemplary embodiments of the invention taken in conjunction with the accompanying drawings.

BRIEF DESCRIPTION OF THE DRAWINGS

Referring now to the drawings which form a part of the original disclosure:

FIG. 8 is a front view of the cutting tool of the internal keratome apparatus shown in FIG. 1 as taken along lines VIII—VIII in FIG. 2;

FIG. 9 is a bottom view of the cutting tool as taken along lines IX—IX in FIG. 8;

FIG. 10 is a top view of the cutting tool as taken along lines X—X in FIG. 8;

FIG. 11 is an enlarged view of the cutting portion of the blade of the cutting tool;

FIG. 12 is a side view of the cutting portion of the blade as taken along lines XII—XII in FIG. 11;

FIG. 13 is another embodiment of the cutting portion of the blade of the cutting tool;

FIG. 14 is a front view of the front portion of the live cornea in which adjacent layers are being separated by the cutting tool of the internal keratome apparatus according to the present invention;

FIG. 15 is a front view of the front portion of the live cornea in which adjacent layers are being further separated by the cutting tool of the internal keratome apparatus according to the present invention;

DETAILED DESCRIPTION OF THE PREFERRED EMBODIMENTS

Figure 1:
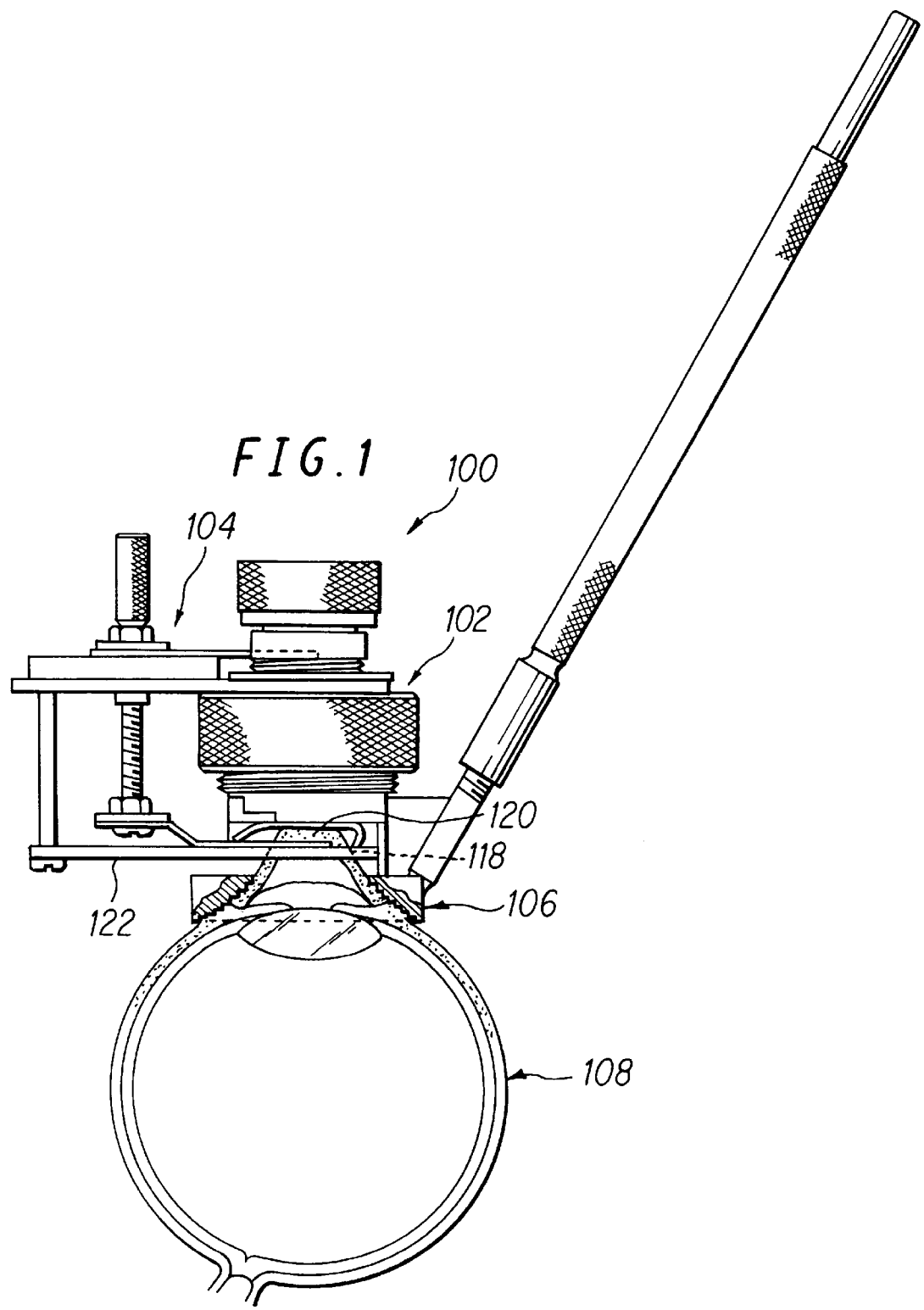
FIG. 1 is a side view of an internal keratome apparatus for forming a pocket between adjacent layers of a live cornea according to an embodiment of the present invention.

An embodiment of an apparatus for performing an internal keratome on a patient's live cornea is illustrated in FIG. 1. Specifically, the apparatus 100 includes a cornea holding apparatus 102 and a cutting tool 104. The corneal holding apparatus 102 and cutting tool 104 are shown in more detail in FIGS. 2–13.

Figure 3:
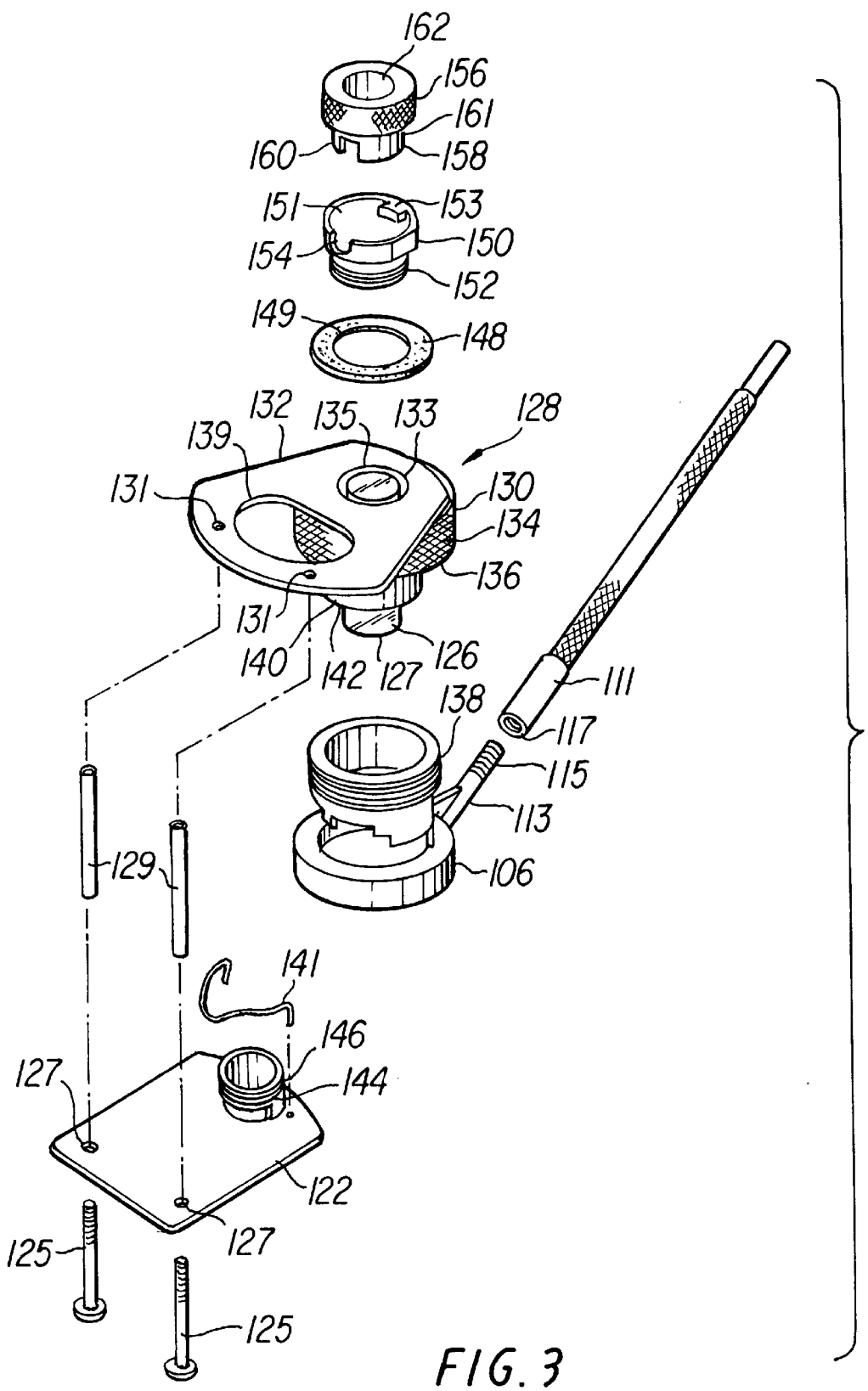
FIG. 3 is an exploded perspective view of the cornea holding apparatus shown in FIGS. 1 and 2.

The corneal holding apparatus 102 includes a cornea receiving section 106 which receives a front portion of a live cornea 108 of a patient's eye as shown, for example, in FIG. 1. Specifically, a tube 110 having an opening 112 therein extending along the length thereof is coupled to the cornea receiving section 106 such that the opening 112 communicates with an interior cavity 114 of the cornea receiving section 106. As shown in FIG. 3, the tube 110 has a section 111 that is removably attached to a section 113 that is secured to or integral with the cornea receiving section 106. In particular, the section 113 has a threaded portion 115 which engages with threads 117 on the interior of section 111 to couple sections 111 and 113 together.

Figure 7:
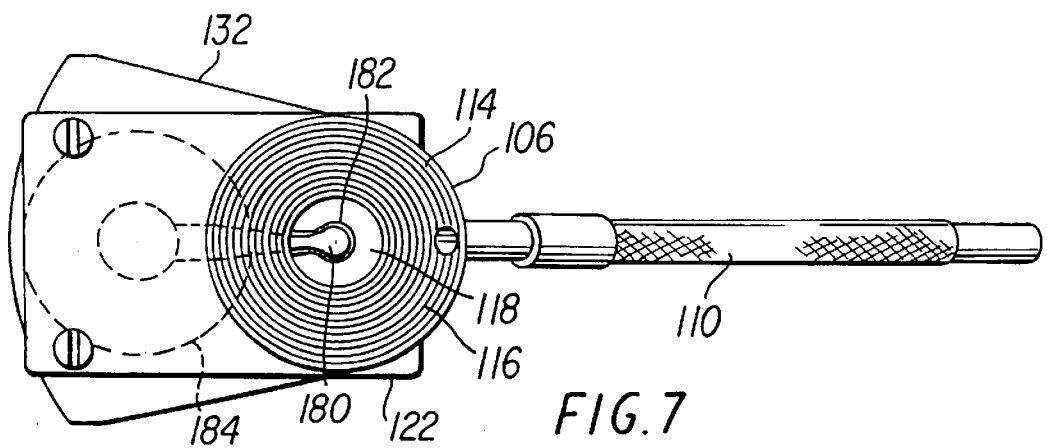
FIG. 7 is a bottom view of the internal keratome apparatus as taken along lines VII—VII in FIG. 6.

As shown in FIG. 7, in particular, the interior surface of the cornea receiving section 106 includes a plurality of steps or ridges 116 which contact the surface of the live cornea 108 and assist in stabilizing the cornea from movement when the cornea is received in the cornea receiving section 106. That is, as the front surface of the cornea 108 of the eye is received in the receiving section 106, suction will be applied via tube 110 to the internal cavity 114 of the receiving section 106 to suck the cornea into the cavity 114.

The cornea receiving section 106 further includes an opening 118. As shown, for example, in FIG. 1, a front portion 120 of the cornea 108 will protrude through the opening 118 when suction is applied to the cavity 114 of the cornea receiving section 106.

The cornea holding apparatus 102 further includes a flat or substantially flat plate 122 having an opening 124 therein. The opening 124 is aligned with or substantially aligned with the opening 118 in the cornea receiving section 106. Hence, as shown in FIG. 1, when the cornea 108 is sucked into the cavity 114 of the cornea receiving section 106, the front portion 120 of the cornea will protrude through the opening 118 in the section 106 and the opening 124 in the plate 122.

The cornea holding apparatus 102 further includes a clear or substantially clear viewer 126 that is mounted in a viewer holding section 128. The viewer 126 is preferably a synthetic material, such as an acrylic, plexy glass, or the like, having threads which are as fine as possible. The viewer 126 is permanently or removably mounted in the viewer holding section 128. The viewer holding section 128 includes a threaded rotating portion 130 and a flat or substantially flat plate 132. The rotating portion 130 is rotatable with respect to the view piece 126 and the plate 132 about an axis the same or substantially the same as the axis of the viewer 126.

The outer surface of the rotating piece 130 preferably has cross-hatching 134 to enable a user of the apparatus 102 to more easily grasp the outer surface of the rotating portion 130. The rotating portion further includes threading 136 on the inner surface thereof. The threading 136 is adaptable to mate with threading 138 of the cornea receiving section 106 as shown specifically in FIG. 3. Hence, the viewer receiving section 128 can be rotatably secured to the cornea receiving section 106 through the engagement of threads 136 and 138 as the rotating portion 130 is rotated onto the threaded portion 138.

The plate 132 further includes a cylindrical or substantially cylindrical section 140 having threads 142 on the interior surface thereof. The plate 122 further includes a protruding section 144 having threads 146 which are adaptable to mate with the threads of the projecting portion 140. Hence, when the plate 132 and thus the protruding portion 140 is rotated about an axis equal to or substantially equal to the axis of the viewer 126, the threads 142 will engage with the threads 146 to pull the plate 132 closer to the plate 122. By doing so, the position of the bottom surface 127 of the viewer 126 with respect to the top surface 123 of the plate 122 can be adjusted.

It is noted that pins 125 are adaptable to be inserted through openings 127 in the flat plate 122 and through hollow pins 129 and into openings 131 of the flat plate 132 so as to assist in coupling the flat plate 132 to the flat plate 122. Furthermore, flat plate 132 includes an opening therein which has any shape suitable to accommodate the cutting tool 104 as will be discussed below.

The cornea holding apparatus 102 further includes a washer 148 made of rubber, synthetic, or the like, and a ring-like member 150 having threads 152 at a bottom portion thereof and an opening 154 therein. The threads 152 are adaptable to mate with threads 133 in an opening 135 of the plate 132. Hence, when the ring-like member 150 is rotated when the threads 152 contact the threads 133, the ring-like member 150 is rotatably secured to the plate 132.

Figure 2:
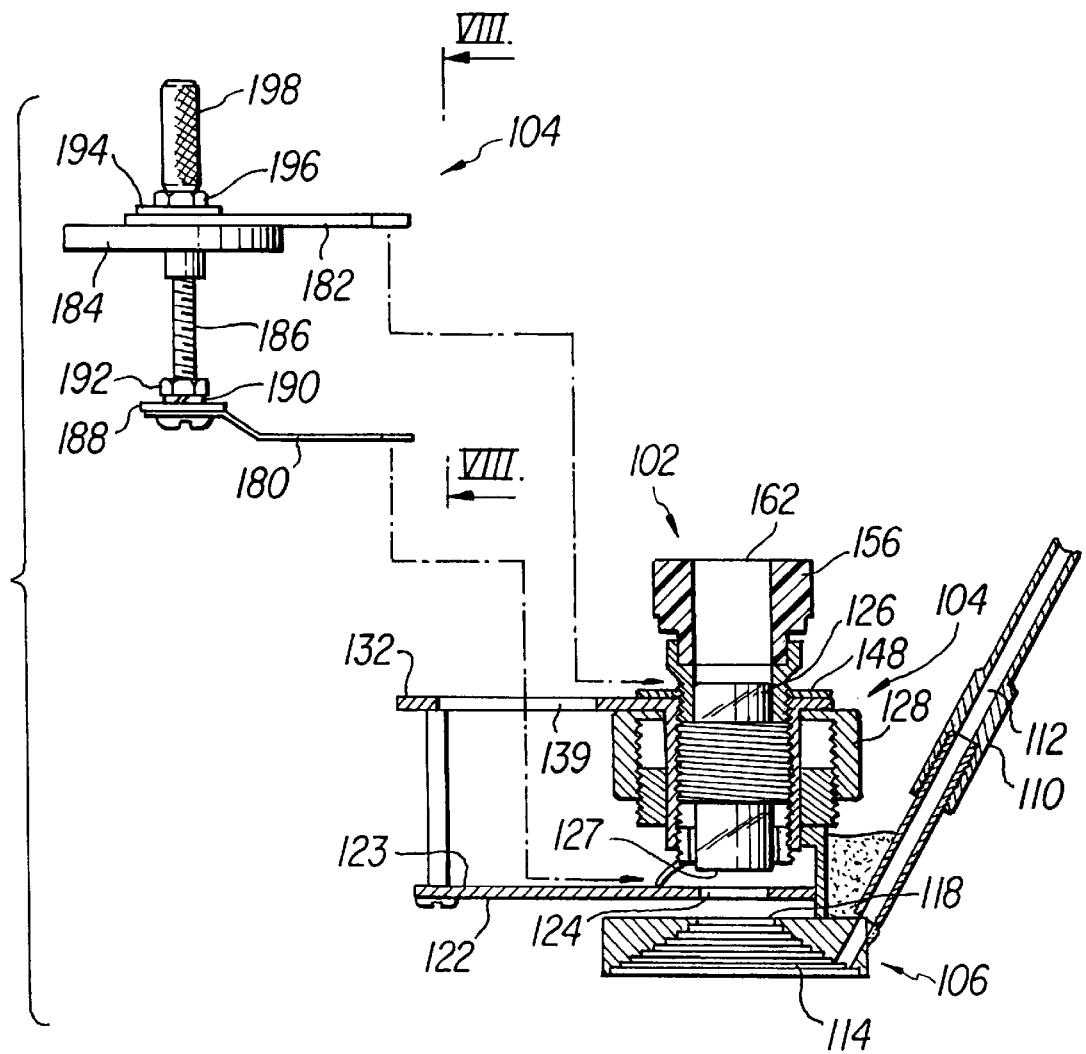
FIG. 2 is a cross-sectional view of the cornea holding apparatus of the internal keratome apparatus shown in FIG. 1 in relation to the cutting tool of the internal keratome apparatus.

The apparatus 102 further includes a second ring-like member 156 made of synthetic, plastic, or the like. The second ring-like member 156 has a protruding portion 158 having an opening 160 therein. The protruding portion 158 is adaptable to be received in an opening 151 of the ring-like member 150 such that the opening 160 is positioned to align with or substantially align with the opening 154. In order to facilitate alignment, the ring-like member 150 includes a notch 153 that is adaptable to engage with an opening 161 in the protruding portion 158 of the second ring-like member 156. The second ring-like member 156 further includes an opening 162 therein. Accordingly, as shown in FIG. 2 specifically, the opening 162, opening 151, an opening 149 in the washer 148, and the viewer 126 are aligned with or essentially aligned with each other so that the surface 120 of the cornea can be seen through the opening 162.

It is noted that except for the viewer 126, washer 148 and second ring-like member 156, all of the components of the cornea holding apparatus 102 are made of metal, steel or the like. Naturally, all components of the cornea holding apparatus can be made of any suitable material as would be readily appreciated by one skilled in the art.

Figure 4:
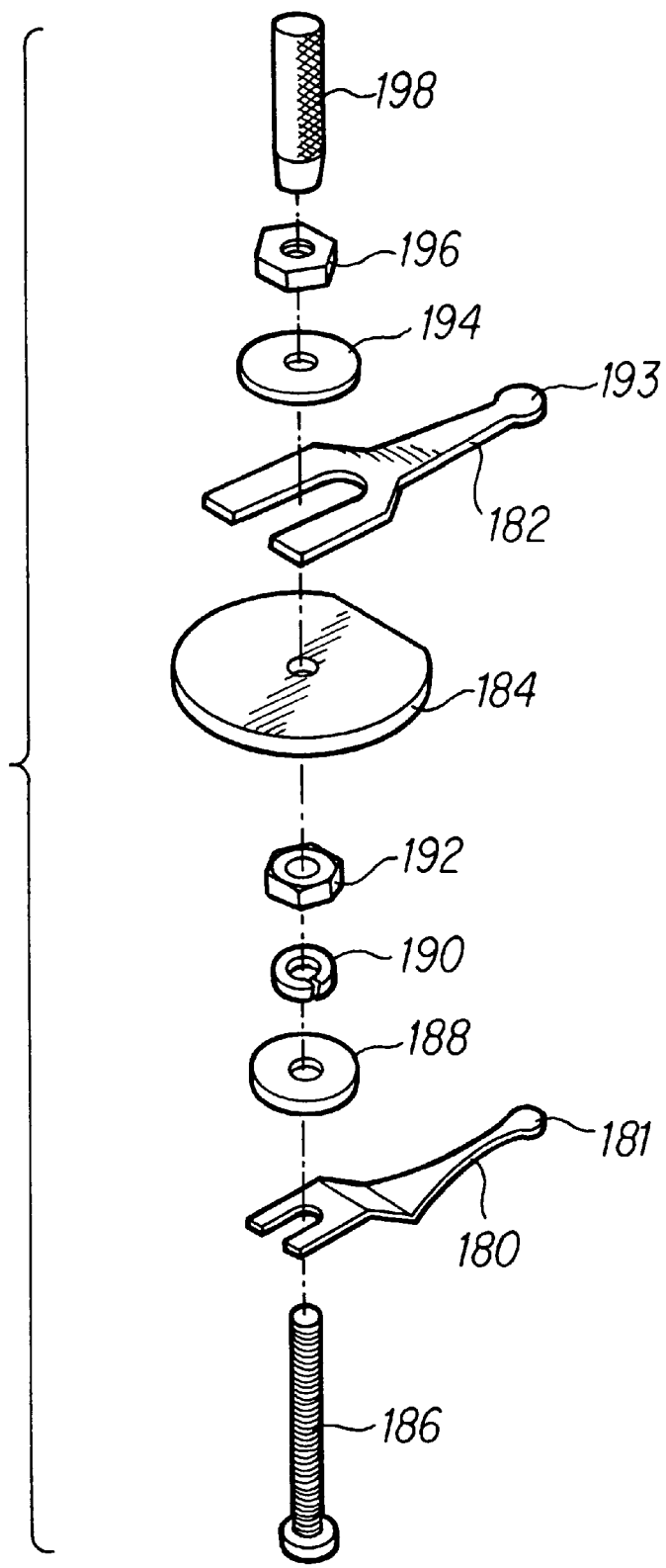
FIG. 4 is an exploded perspective view of the cutting tool shown in FIGS. 1 and 2.

Turning now to the cutting tool 104, as shown in FIG. 4, the cutting tool 104 includes a blade 180, a guiding device 182, and a flat plate 184. The blade 180, the guiding device 182 and the plate 184 are coupled together, for example, by a screw 186, washer 188, washer 190, nut 192, washer 194, nut 196 and a handle 198 having cross-hatching thereon to enable its outer surface to be gripped more easily. As shown in FIG. 9 specifically, the blade 180 and the guiding member 182 are aligned or essentially aligned with each other.

The operation of the apparatus 100 will now be described. As shown in FIGS. 1 and 2 specifically, the cutting tool 104 is removably attached to the cornea holding apparatus 102 such that the front end 183 of the guide member 182 is inserted through the opening 160 of the ring-like member 156 and through the opening 154 of the ring-like member 150. Furthermore, the front end 181 of the blade 180 is adaptable to be inserted between the bottom surface 127 of the viewer 126 and the top surface 123 of the flat plate 122.

In coupling the cutting tool 104 to the cornea holding apparatus 102, the blade 180, screw 186, washers 188 and 190, and nut 192 are inserted through the opening 139 in the plate 132 as illustrated specifically in FIG. 2. Accordingly, when suction is applied to the cornea of the eye 108, the front surface 120 of the cornea is forced to protrude through the opening 118 in the receiving section 106 and the opening 124 and the flat plate 102 so that the cornea 120 contacts the bottom surface 127 of the viewer 126. Hence, the front surface 120 of the cornea will become flattened to a certain degree due to the contact with the surface 127 of the viewer 126.

When layers of the live cornea are to be separated, the front end 181 of the blade 180 will be directed toward the protruding portion 120 of the cornea to be inserted into the protruding portion 120 and thus separate adjacent layers of the cornea 108 from each other. As shown in FIGS. 11 and 12 specifically, the front end portion 181 of the blade 180 is round or substantially round such that its diameter is about 4 mm. and is greater than the width of the blade and change "181" to 180. The blade 180 can be any desired shape, such as star-shaped, petal shaped, oval, or the like, which can be adapted to form a circularly shaped or substantially circularly shaped pocket between the layers of the live cornea. The blade can be made of any type of suitable material such as surgical steel, stainless steel or the like, and can have a diamond cutting edge. The cutting edge 183 should be at the top surface of the portion 181. The top surface 185 and bottom surface 187 of the blade can be parallel or substantially parallel with each other.

Alternatively, as shown in FIG. 13, the front portion 181 can be slanted as indicated by 181'. In this event, the cutting edge 183' of the blade is formed by the contact between the slanted surface 185' and the bottom surface 187 of the blade.

Figure 5:
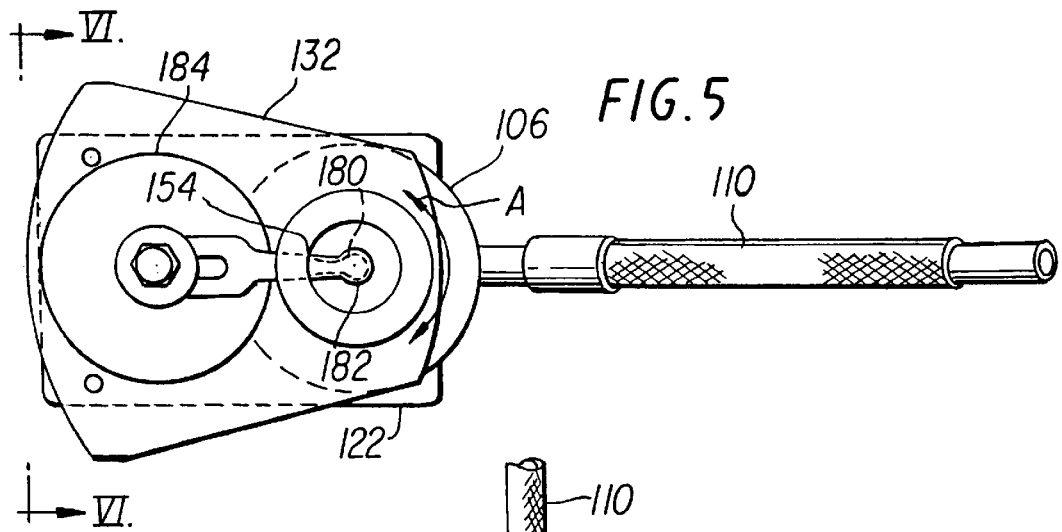
FIG. 5 is a top view of the internal keratome apparatus as taken along lines V—V in FIG. 1.
Figure 6:
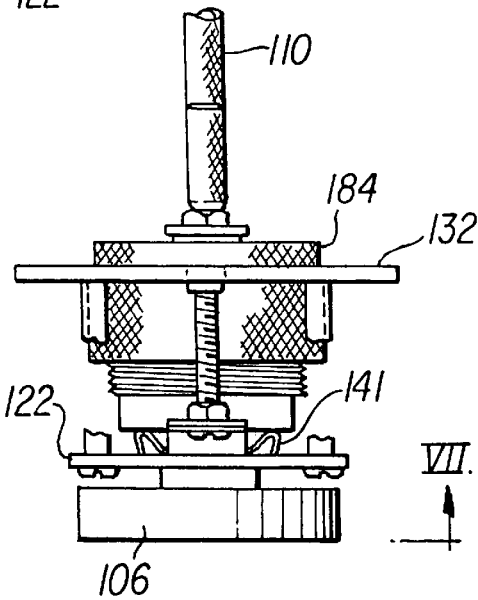
FIG. 6 is a front view of the internal keratome apparatus as taken along lines VI—VI in FIG. 5.

As shown in FIGS. 5 and 7, the blade 180 will be aligned with or substantially aligned with the guide member 182. Hence, the position of the guide member 180 with respect to the front surface of the protruding portion 120 of the live cornea that is being flattened by the bottom surface 127 of the viewer 126 will correspond to or substantially correspond to the position of the blade 182 with respect to the protruding portion of the live cornea. A spring member 141 which is integral or attached to the flat plate 122 will function to urge the blade 180 toward the top surface 123 of the plate 122. Hence, the bottom surface 187 of the blade 180 will contact the top surface 123 of the plate 122 while the spring 141 contacts the top surface 185 of the blade 180.

The cutting tool 102 can then be moved to form a pocket between adjacent layers of the live cornea.

Specifically, as shown in FIG. 14, when the blade 180 is being inserted into the front surface 120 of the live cornea, an incision or separation 200 between adjacent layers of the live cornea will be formed. As the blade 180 is further inserted into the front surface 120 of the cornea, the spacing between the layers of the live cornea will be expanded to form a space 202 as shown in FIG. 15. The blade 180 can then be moved by twisting the handle 198 so that the blade 180 will reciprocate in a direction along arrow A. By moving the blade 180 in this reciprocating manner, the front portion of the blade 181 will form a circularly-shaped or substantially circularly-shaped pocket 206 in the front surface 120 of the cornea. The pocket 206 can be made at any practical size as desired. Furthermore, the pocket 206 can be made at any practical depth in the front surface 120 of the live cornea.

Specifically, the depth at which the pocket will be formed in the cornea 108 is governed by the distance between the top surface 185 of the blade 180 and the bottom surface 127 of the viewer 126. That is, since the thickness of the blade 180 is known, the distance between the bottom surface 127 of the viewer 126 and the top surface 123 of the flat plate 122 is set so that the cutting edge 183 of the blade will enter the front protruding portion 120 of the cornea at the desired distance from the front surface of the live cornea (i.e., at the desired depth into the live cornea).

The distance between the bottom surface 127 of the viewer 126 and the top surface 123 of the plate 122 can be adjusted when the viewer holding section 128 is being attached to the plate 122 in the manner discussed above. That is, the amount that the cylindrical portion 140 is screwed onto the protruding portion 144 as shown in FIG. 3 will determine the distance between the front surface 127 of the view-piece 126 and the top surface 123 of the plate 122. Hence, the cylindrical portion 140 will be threaded onto the protruding portion 144 to a degree that will space the front surface 127 of the viewer 126 from the top surface 123 of the plate 122 the desired distance.

It is noted that the range in which the guide member 182 will reciprocate along the direction indicated by arrow A in FIG. 5 will be limited by the width of the opening 154 in ring member 150. That is, if the pocket 206 is to be made larger in a direction transverse to the extending direction of the blade 180, the width of the opening in ring member 150 will be larger to enable the guide member 182 to reciprocate along a larger arc in the direction defined by arrow A. Accordingly, because the blade 180 is aligned or substantially aligned with guide member 182, the blade will also be able to reciprocate along an arc in the direction defined by arrow A as limited by the width of the opening 154 in the ring-like member 150. Hence, different ring-like members having differently sized openings 154 can be used to adjust the size of the pocket 206 formed in the front portion 120 of the cornea.

It is noted that if desired, an implant, such as those discussed above, can be placed inside the pocket to alter the curvature of the cornea.

Figure 17:
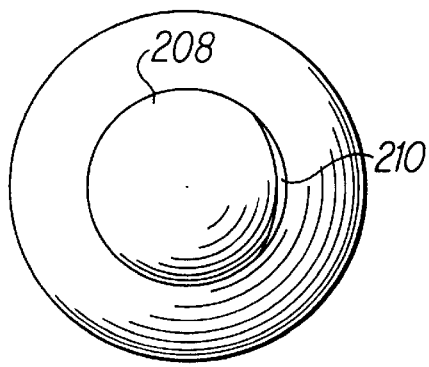
FIG. 17 is a front view of the front portion of the live cornea in which the pocket formed in the live cornea as shown in FIG. 16 is expanded by the cutting tool to form a flap-like layer at the front portion of the live cornea.

Also, if it is desirable to separate the front layer of the cornea 108 so that the front layer becomes a flap-like layer, the distance along which the guide member 182 and hence, the blade 180, are allowed to reciprocate can be increased to form this flap-like layer as shown, for example, in FIG. 17. That is, the guide member 182 can be allowed to reciprocate along an arc large enough to allow the cutting portion 181 of the blade 180 to pass through the sides of the front protruding portion 120 of the cornea as necessary so that the flap-like layer 208 is separated from the main portion of the live cornea except for a connecting portion 210.

Accordingly, the flap-like layer 208 will be capable of pivoting with respect to the remaining portion of the live cornea 108 about connecting portion 210 to expose a surface of the cornea underneath the flap-like layer 208. That exposed surface can be irradiated with a laser, for example, as described in U.S. Pat. No. 4,840,175 to Peyman, the entire contents of which are incorporated herein by reference. Also, a ring or disc can be placed on the exposed surface of the cornea and then covered by the flap-like layer 208 so that the shape of the ring or disc will influence the shape of the flap-like layer and hence, change the refractive power of the flap-like layer, thereby changing the focusing power of the eye.

It is noted that forming the pocket prior to forming the flap-like layer, protects the eye from losing aqueous humor if the blade 180 is inadvertently inserted too deep into the cornea so that it enters the anterior chamber of the eye. That is, because the pocket is only open on one end, as contrasted with a flap which is essentially separated from the cornea but for the connecting portion 210, the pocket will function to retain fluid in the anterior chamber and thus prevent against fluid loss better than would a flap-like member.

Figure 19:
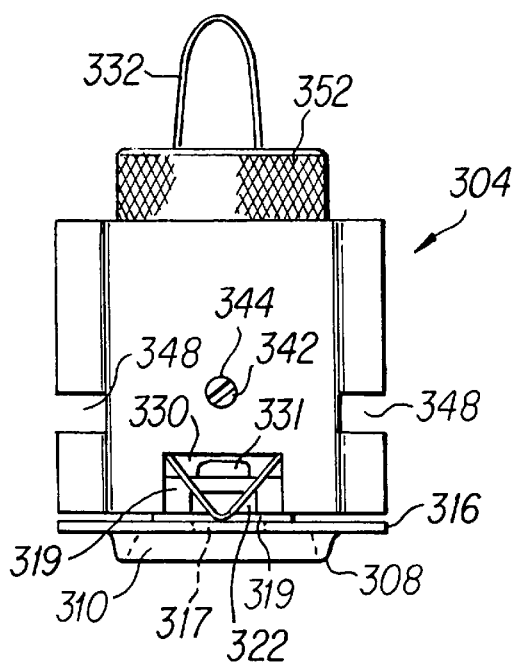
FIG. 19 is a front view of the embodiment of the cornea holding apparatus shown in FIG. 18 as taken along lines XIX—XIX.
Figure 20:
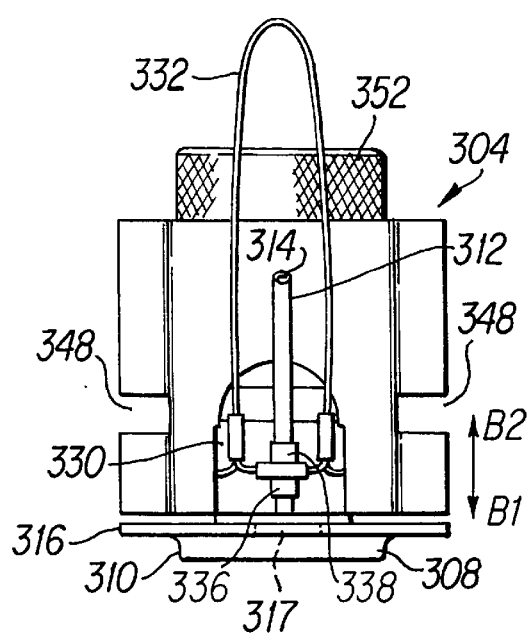
FIG. 20 a rear view of the embodiment of the cornea holding apparatus shown in FIG. 18 as taken along lines XX—XX.
Figure 18:
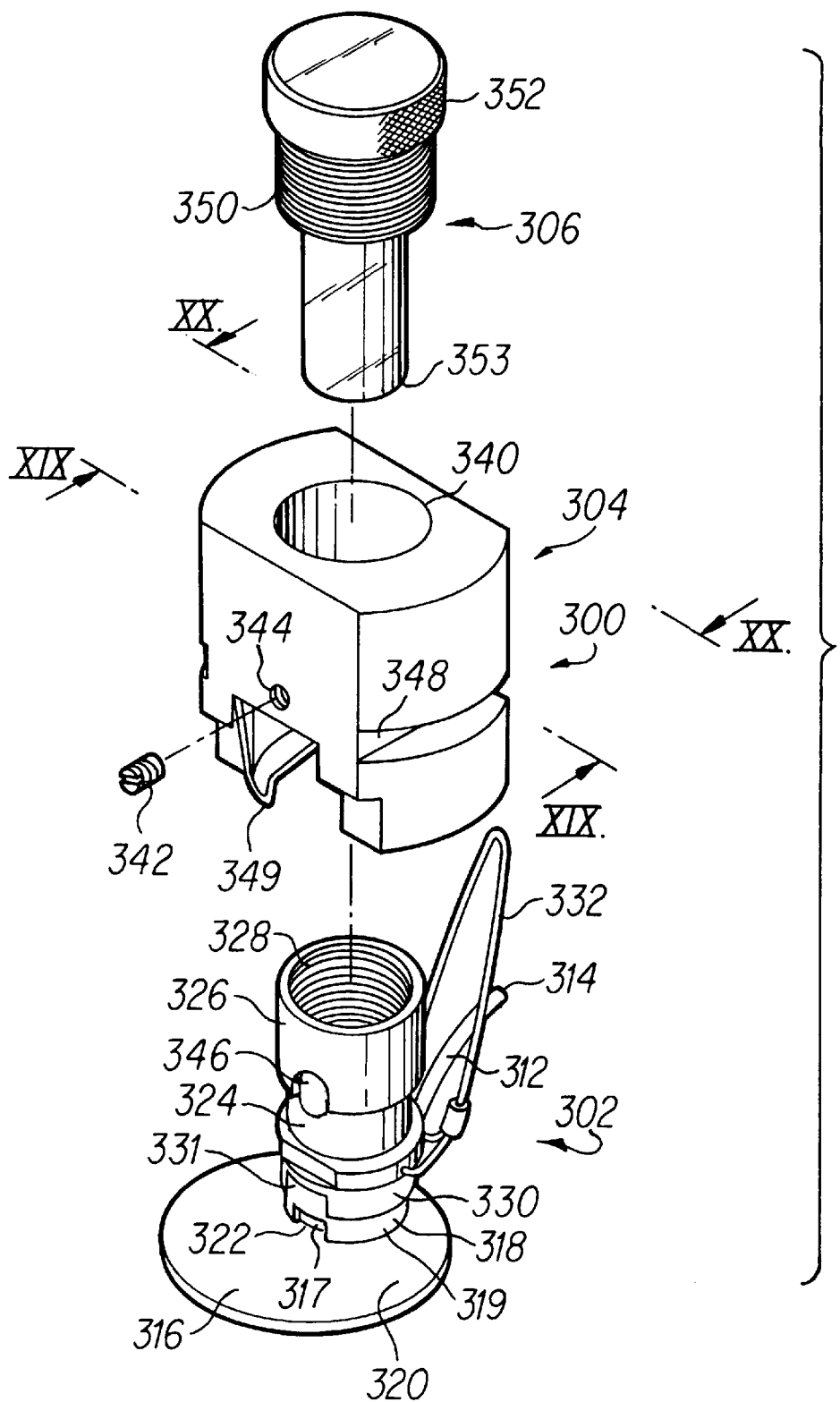
FIG. 18 is an exploded perspective view of another embodiment of a cornea holding apparatus of an internal keratome apparatus according to the present invention.

Another embodiment of the cornea holding apparatus of the present invention is shown, for example, in FIGS. 18–20. Specifically, the apparatus 300 includes a cornea holding section 302, a body 304 and a viewer 306. The cornea holding section 302 includes a cornea receiving section 308 having a cavity 310. A hollow tube 312 having an opening 314 along the length thereof is in communication with the cavity 310.

The cornea holding apparatus 302 further includes a flat plate 316 that is either attached to or integral with the cornea receiving section 310. A tubular extension 318 extends in a direction away from the top surface 320 of the flat plate 316. The narrow section 319 of the tubular extension 318 adjacent to the top surface 320 of the flat plate 316 has an opening 322 therein. Furthermore, the flat plate 316 has an opening 317 therein which communicates with the cavity 310 of the cornea receiving section 308.

The tubular extension 318 further has a first wider section 324 having an outer diameter greater than that of the narrow section, and a second wider section 326 having an outer diameter greater than that of the first wider section 324. The second wider section 326 has threading 328 along the inner circumference thereof. The tubular extension 318 is hollow throughout so that the interior of the second wider section 326 is in communication with the interior of the first wider section 324, the interior of the narrow section 319, the opening 322 and the opening 317 in the flat plate 316. Hence, the interior of the tubular extension 318 is in communication with the cavity 310 of the cornea receiving section 308.

A ring-like member 330 is positioned about the tubular extension 318 and is coupled to a handle 332. As can be appreciated by one skilled in the art and described in more detail below, the handle 332 can be configured to move the ring-like member 330 down and up along the tubular extension 318 in the directions indicated by arrows B1 and B2, respectively. When the ring-like member 330 is moved downward in the direction B1, the opening 331 in the ring-like member 330 will align or substantially align with the opening 322 in the tubular extension 318.

As illustrated in FIG. 18, the cornea holding section 302 is received in an opening 340 of the body 304. The opening 340 extends throughout the center of the body 304 such that the body will substantially encase the tubular member 318. A screw 342 can be received in a threaded opening 344 in the body 304 to abut against the screw contacting surface 346 of the cornea receiving section 302 to thus removably secure the body 304 to the cornea receiving section 302. The body 304 further includes recesses 348 which extend on opposite sides thereof as illustrated.

The viewer 306 is made of a synthetic material, such as acrylic or the like, and is transparent or substantially transparent to visible light. The viewer 306 has threads 350 which engage with the threads 328 of the cornea receiving section 302 when the viewer 306 is inserted into the opening 340 of the body 304, and thus into the opening in the second wider section 326 of the tubular projection 318 as illustrated. Accordingly, the viewer 306 is threadedly engaged with the cornea receiving apparatus 302. The threads 352 on the viewer 306 enable a user to grip the outer surface of the viewer 306 more firmly and thus, screw the viewer 306 into the tubular extension 318.

Figures 21, 23:
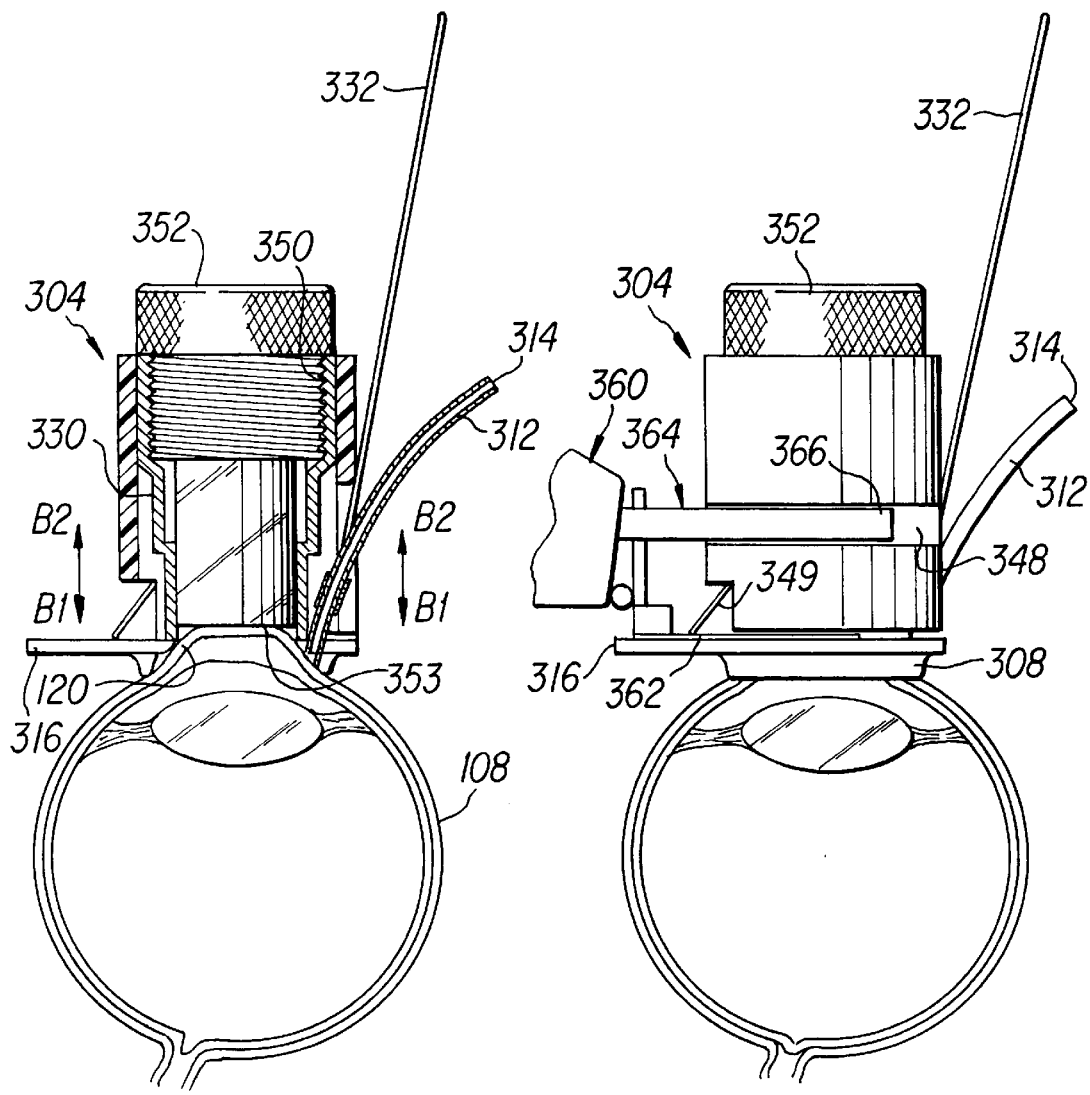
FIG. 21 is a cross-sectional view of the cornea holding apparatus shown in FIGS. 18–20.
FIG. 23 is a side view of the embodiment of the cutting tool apparatus shown in FIG. 22 engaging with the cornea holding apparatus shown in FIGS. 18–21.

The operation of the apparatus 300 will now be described with reference to FIGS. 21–28, in particular. Specifically, as shown in FIG. 21, when a cornea 108 is received in the cornea receiving section 308 and suction is applied via tube 312 to the cavity 310, the cornea will be sucked into the cavity 310. However, a front portion 120 of the cornea will protrude through the opening 317 in the plate 316. Preferably, the viewer 306 will be adjusted so that the bottom surface 353 of the viewer contacts the front surface of the cornea 108 to flatten out the front surface of the front portion 120 of the cornea as illustrated.

Figure 22:
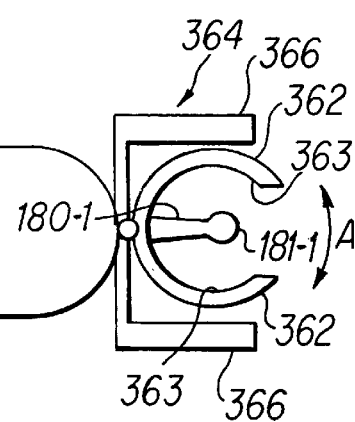
FIG. 22 is a top view of another embodiment of a cutting tool used of an internal keratome apparatus according to the present invention.

In order to separate layers of the live cornea from each other, a tool 360 as shown in FIG. 22 can be used. Specifically, the tool 360 includes a blade 180-1 having a cutting portion 181-1 as described above with regard to FIG. 11. The tool 360 includes a motor which functions to move the blade 180-1 in a reciprocal motion along arrow A as illustrated. The blade can also be shaped as the blades described above with regard to FIGS. 12 and 13, for example, and can be made of the materials described above. The blade 180-1 has a top surface 185-1, a bottom surface 187-1, and a cutting edge 183-1, as shown in FIG. 12. Also, as shown in FIG. 13, the front portion 181'-1 can be slanted, with the cutting edge 183'-1 formed by the contact between the slanted surface 185'-1 and bottom surface 187'-1.

As shown in FIG. 23, if layers of the live cornea in the front protruding portion 120 are to be separated from each other by the blade 180-1, the tool 360 will be positioned so that the rails 362 of the tool 360 are positioned about the tubular extension 318. It is noted that a spring-like member 349 of the body 304 will press against the top surface 185-1 of the blade 180-1 when the blade 180-1 is being positioned as shown in FIG. 23 so that the bottom surface 187-1 of the blade will contact the top surface 320 of the plate 316. The cutting or separating of the layers, as illustrated in FIGS. 14–17, can then be performed as follows.

Figure 16:
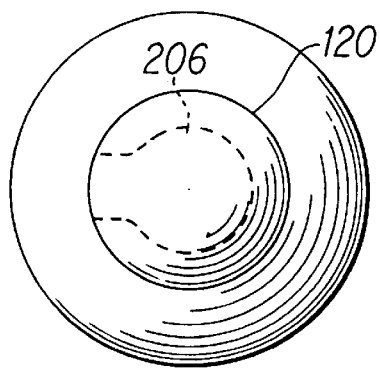
FIG. 16 is a front view of the front portion of the live cornea in which adjacent layers are being separated by the cutting tool of the internal keratome apparatus according to the present invention such that a circularly-shaped or substantially circularly shaped pocket is formed between the adjacent layers of the live cornea.
Figure 24:
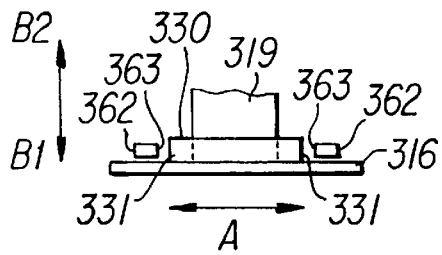
FIG. 24 is a view of the ring-like member of the cornea holding apparatus shown in FIGS. 18–21 and 23 as positioned in its lower position.

Specifically, if it is desirable to separate adjacent layers of the cornea so that a pocket 206 is ultimately formed between those adjacent layers as shown in FIG. 16, the handle 332 is positioned so that the ring-like member 330 moves in the direction B1 and becomes positioned to touch or substantially touch the top surface 320 of the plate 316 as shown in FIG. 24. In this event, the reciprocal motion of the blade 180 along the direction A is limited by the contact of the inner surface 363 of the rails 362 and the outer surface 333 of the ring 330.

Figure 26:
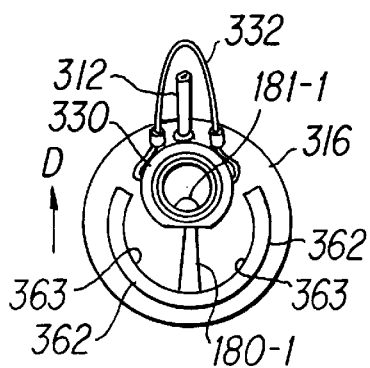
FIG. 26 is a view of the guide rails of the cutting tool apparatus shown in FIG. 22 engaging with the ring-like member of the cornea holding apparatus shown in FIGS. 18–21 and 23 when the blade is positioned at a first depth in the cornea.
Figure 27:
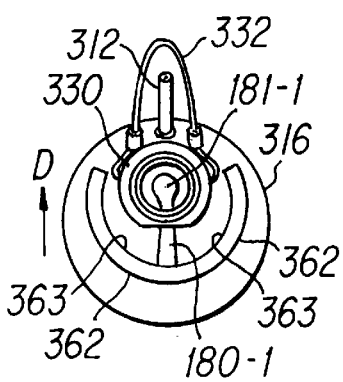
FIG. 27 is a view of the guide rails of the cutting tool apparatus shown in FIG. 22 engaging with the ring-like member of the cornea holding apparatus shown in FIGS. 18–21 and 23 when the blade is positioned at a second depth in the cornea.
Figure 28:
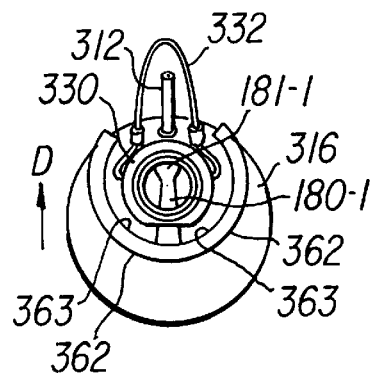
FIG. 28 is a view of the guide rails of the cutting tool apparatus shown in FIG. 22 engaging with the ring-like member of the cornea holding apparatus shown in FIGS. 18–21 and 23 when the blade is positioned at a third depth in the cornea.

Accordingly, as the blade is moved in the direction D as shown in FIGS. 26–28, while the blade 180-1 is reciprocated by the tool 360 in a reciprocating direction A, the separations 200, 202 and 206 between adjacent layers of the cornea as shown in FIGS. 14–16, respectively, will be formed. As illustrated in FIG. 23, the reciprocating tool can include a guide 364 having guide rails 366 which each engage with the respective grooves 348 which are on opposite sides of the body 304 so as to assist in guiding the blade 180 in the direction D.

Hence, when the blade is positioned as shown in FIG. 26, the space 200 shown in FIG. 14 will be formed. When the blade is then moved to the position shown in FIG. 27 and ultimately to the position shown in FIG. 28, the space 202 between the layers of the cornea as shown in FIG. 15 will be formed, and then the pocket 206 as shown in FIG. 16 will be formed. As can be appreciated from FIGS. 26–28, due to the curved shape of the rails 362, the reciprocal movement of the blade 180-1 in the direction A will be limited more when the blade is positioned as shown in FIG. 26 than when the blade is positioned as shown in FIG. 27. Also, the movement of the blade 180-1 in the reciprocal direction A will be limited more due to the curvature of the rails 362 when the blade 180-1 is in the position as shown in FIG. 28 than when the blade 180-1 is in the position as shown in FIG. 27. Accordingly, a circularly-shaped pocket 206 as shown in FIG. 16 can be formed.

It is further noted that the depth at which the blade 180-1 will cut into the cornea is determined based on the distance between the bottom flat surface 353 of the viewer 306 and the top surface 320 of the plate 316. That is, taking into account the thickness of the blade 180-1, the viewer 306 can be screwed into the tubular extension 318 to a depth necessary so that the distance between the bottom surface 353 of the eye-piece and the top surface 320 of the plate 316 will position the blade 180-1 to enter into the cornea 108 at the desired depth from the front of the cornea 108 when the front of the cornea contacts the bottom surface 353 of the viewer 306.

Figure 25:
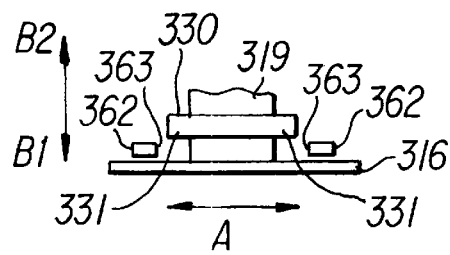
FIG. 25 is a view of the ring-like member of the cornea holding apparatus shown in FIGS. 18–21 and 23 as positioned in its upper position.

It is further noted that if it is desirable to form a flap-like layer 208 as shown in FIG. 17, the ring 330 which restricts the reciprocating motion of the blade can be lifted as shown in FIG. 25. That is, as discussed above, the handle 332 can be moved so that the ring-like member 330 will slide about the tubular extension 318 in the direction toward position B2. Hence, the inner surfaces 363 will no longer contact the outer surface 331 of the ring-like member 330. Rather, the movement of the blade 180-1 will be limited by the contact of the inner surfaces 363 of the rails 362 and the outer surface of the tubular extension 318. Because the outer circumference of the tubular member 318 is smaller than the outer circumference of the ring-like member 330, the movement of the blade 180-1 will be less restricted in the direction A because the rails 362 will be allowed to move a greater direction along the direction A.

Accordingly, the cutting portion 181-1 of the blade 180-1 will cut through the sides of the front portion 120 of the cornea to form a flap-like layer 208 that is connected to the remainder of the cornea by a connection portion 210. As discussed above, the flap-like layer 208 can be lifted to expose an inner surface of the cornea, and various techniques can be performed on that inner surface of the cornea.

Additionally, when the blade 180-1 is inserted in the cornea 108, it may be necessary to remove corneal epithelium prior to performing the cutting so that the corneal epithelium cells do not become attached to the blade 180 and be forced by the blade between the adjacent layers of the cornea. In other words, it may be necessary to remove the corneal epithelium so that those cells do not become lodged in the pocket 206.

Figure 29:
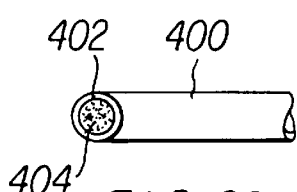
FIG. 29 is a perspective view of an embodiment of an instrument for use in removing epithelial cells from the outer surface of a live cornea according to the present invention.

In order to remove the corneal epithelium cells prior to performing the cutting, an instrument 400 as shown in FIG. 29 can be used. The instrument 400 can be a tube-like structure having a hollow opening 402 therein in which is disposed a sponge 404 which is made of rubber or the like. The inner diameter of the tube can be, for example, about 1–12 millimeters. If it is determined desirable to remove the corneal epithelium cells prior to performing the cutting or layer separating operation discussed above, the end of the instrument 400 in which the sponge 404 is disposed can be dipped into an alcohol mixture so that the alcohol mixture will become absorbed in the sponge 404. The end of the instrument 400 having the sponge 404 can then be dabbed onto the front portion 120 of the cornea that is to be cut, thus eliminating the epithelium cells.

As shown in table 1 set forth below, the time for which the instrument 400 must be applied to the front portion 120 of the cornea depends on the concentration of the alcohol in the mixture.

TABLE 1

| Alcohol Concentration | Duration of Application of Instrument |
| --- | --- |
| 50 percent | 10 seconds |
| 30 percent | 15 seconds |
| 20 percent | 20 seconds |
| 15 percent | 30 seconds |
| 10 percent | 45 seconds |

Figure 30:
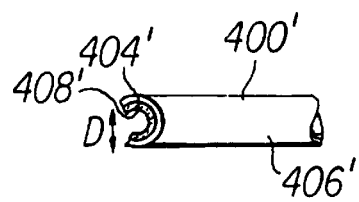
FIG. 30 is a perspective view of another embodiment of an instrument for use in removing epithelial cells from the outer surface of a live cornea according to the present invention.
Figure 31:
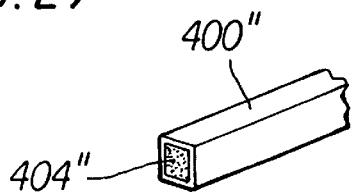
FIG. 31 is a perspective view of a further embodiment of an instrument for use in removing epithelial cells from the outer surface of a live cornea according to the present invention.

As shown in FIGS. 30 and 31, the instrument 400 need not be tubular, but rather, can be arcuate in shape (see FIG. 30) or rectangular or square (see FIG. 31). If the instrument is arcuately-shaped, the diameter D should be about 1–12 millimeters, and the sponge 404' will be inserted between the outer wall 406' and inner wall 408' of the arcuately-shaped instrument 400'. If the square or rectangularly-shaped instrument 400" is used, the sponge 404" also will have a similar shape. If the time at which the instruments 400' or 400" will be applied to the front portion 120 of the cornea prior to cutting the front portion of the cornea will be the same as illustrated in Table 1 depending on the concentration of the alcohol mixture used. Accordingly, the instruments shown in FIGS. 29–31 will prevent the epithelium cells from becoming lodged between the layers of the cornea when the pocket 206 or flap 208, as shown in FIGS. 16 and 17, respectively, are formed by insertion of the blade 180 into the cornea.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. An apparatus for separating a layer from a patient's live cornea, comprising:
    a suction mechanism, adapted to apply suction to a front surface of the live cornea;
    a separating tool, having a separating edge and being adapted to move in a reciprocating motion to form a pocket between the layer of the live cornea and a remaining portion of the live cornea;
    a guiding mechanism, adapted to guide the separating tool in a first direction toward the live cornea to which suction is being applied by the suction mechanism; and
    a restricting device which is adapted to automatically restrict the reciprocating motion of the separating tool to a first reciprocating travel distance, transverse of the first direction, until the separating edge of the separating tool being guided by the guiding mechanism along the first direction reaches a first depth in the live cornea, and then automatically restrict the reciprocating motion of the separating tool to a second reciprocating travel distance, transverse of the first direction and greater than the first reciprocating travel distance, while the separating tool is being guided along the first direction until the separating edge reaches a second depth, greater than the first depth, in the live cornea so that the separating tool forms the pocket in the live cornea when moving between the first and second depths.

2. An apparatus as claimed in claim 1, wherein:
    the separating tool has first and second portions, the first portion having a separating edge which is adaptable to separate the layer from the remaining portion of the live cornea;
    the first and second portions being arranged in a tool extending direction toward the separating edge and transverse to a reciprocating direction along which the separating tool reciprocates; and
    the width of at least some of the first portion taken along the reciprocating direction is larger than the width of the second portion taken along the reciprocating direction.

3. An apparatus as claimed in claim 2, wherein the first portion is substantially circularly shaped with a diameter thereof extending along the reciprocating direction and a rotational axis thereof extending substantially perpendicular to the tool extending direction.

4. An apparatus as claimed in claim 2, wherein:
    the tool has first and second surfaces on opposite sides thereof, each comprising a portion of each of the first and second portions, the first surface being longer than the second surface in the tool extending direction and being adaptable to be positioned closer than the second surface to the front surface of the live cornea when the tool is inserted into the live cornea; and
    the tool further has a third surface disposed at an angle other than 0° with respect to the first surface, the third and first surfaces connecting to form the separating edge.

5. An apparatus as claimed in claim 2, wherein:
    the tool has first and second surfaces on opposite sides thereof, each comprising a portion of each of the first and second portions, the first surface having a first section extending at an angle other than 0° with respect to the tool extending direction.

6. An apparatus as claimed in claim 5, wherein the first surface further has a second section which is substantially parallel with the second surface.

7. An apparatus as claimed in claim 5, wherein the first section is a portion of the first portion and is angled with respect to the second surface such that the distance between the first section and the second surface measured proximate to the separating edge is less than the distance between the first section and the second surface measured at a location along the first section away from the separating edge in a direction opposite to the tool extending direction.

8. An apparatus as claimed in claim 1, wherein the suction mechanism comprises a guiding mechanism adaptable to guide the separating tool toward the live cornea.

9. An apparatus as claimed in claim 1, wherein the suction mechanism comprises a guide adaptable to position the separating tool to form the pocket in the live cornea at a designated distance from the front surface of the live cornea.

10. An apparatus as claimed in claim 1, wherein the suction mechanism comprises a viewing device, adaptable to enable a user to view the front surface of the live cornea to which suction is being applied.

11. An apparatus as claimed in claim 10, wherein the viewing device has a surface adaptable to contact the front surface of the live cornea when suction is being applied to the live cornea.

12. An apparatus as claimed in claim 1, wherein the separating tool is adaptable to be removably attached to the suction mechanism.

13. An apparatus as claimed in claim 1, further comprising a device which is adaptable to be positioned in a first position to restricting the reciprocating motion of the separating tool to cause the separating tool to form the pocket in the live cornea; and
    wherein the device is further adaptable to be positioned in a second position to unrestrict the reciprocating motion of the separating tool to cause the separating tool to expand the pocket in the live cornea to form a flap-like layer at the front surface of the live cornea.

14. An apparatus for forming a substantially circularly shaped pocket between layers of a patient's live cornea, comprising:
    a stabilizing mechanism, adapted to substantially stabilize the live cornea;
    a separating tool, having a separating edge and being adapted to move in a reciprocating motion to form the substantially circularly shaped pocket between layers of the live cornea;
    a guiding mechanism, adapted to guide the separating tool in a first direction toward the live cornea being stabilized by the stabilizing mechanism; and
    a restricting device which is adapted to automatically restrict the reciprocating motion of the separating tool to a first reciprocating travel distance transverse of the first direction, until the separating edge of the separating tool being guided by the guiding mechanism along the first direction reaches a first depth in the live cornea, and then automatically restrict the reciprocating motion of the separating tool to a second reciprocating travel distance, transverse of the first direction and greater than the first reciprocating travel distance, while the separating tool is being guided along the first direction until the separating edge reaches a second depth, greater than the first depth, in the live cornea, so that the separating tool forms the substantially circularly shaped pocket in the live cornea when moving between the first and second depths.

15. An apparatus as claimed in claim 14, wherein the separating tool has a substantially circularly shaped blade adaptable for forming the substantially circularly shaped pocket.

16. An apparatus as claimed in claim 14, wherein the stabilizing mechanism further comprises a device, adaptable to restrict the reciprocating movement of the blade to cause the blade to form the pocket between the layers of the live cornea; and the device is further adaptable to unrestrict the reciprocating movement of the blade to enable the blade to expand the pocket to form a flap-like layer at the front of the live cornea.

17. An apparatus as claimed in claim 14, wherein the stabilizing mechanism is adaptable to apply suction to the front surface of the live cornea to stabilize the live cornea.

18. A method for separating a front layer of a patient's live cornea from a remainder of the live cornea, comprising the steps of stabilizing the live cornea to substantially restrict the live cornea from moving;

inserting a separating tool into the live cornea at a first depth;

while the separating tool is at the first depth, moving the separating tool in a reciprocating motion, transverse the optical axis of the live cornea and automatically restricting said reciprocating motion to a first reciprocating travel distance, to separate a portion of the front layer of the live cornea from a portion of an adjacent layer of the live cornea to form a space between the front and adjacent layers defined by edges of other portions of the front and adjacent layers which remain attached to each other, the space having a length extending between two of the edges in a direction transverse to an optical axis of the live cornea;

moving the separating tool from the first depth to a second depth in the live cornea; and while the separating tool is moving from the first depth to the second depth, moving the separating tool in said reciprocating motion, and automatically restricting said reciprocating motion to a second reciprocating travel distance greater than said first reciprocating travel distance, to separate sections of the other portions of the front and adjacent layers of the live cornea from each other to form a pocket between the front and adjacent layers which is defined by new edges of the other portions of the front and adjacent layers which remain connected, such that the pocket has a length extending between two of the new edges in a direction transverse to the optical axis of the live cornea, the length of the pocket being greater than the length of the space.

19. A method as claimed in claim 18, wherein the inserting step comprises the step of:

while the separating tool is at the first depth in the live cornea, moving the separating tool in a reciprocating motion, transverse to the optical axis of the live cornea, to separate the portion of the front layer from the portion of the adjacent layer of the live cornea to form the space between the front and adjacent layers.

20. A method as claimed in claim 18, further comprising the steps of:

moving the separating tool from the second depth to a third depth in the live cornea; and while the separating tool is at the third depth, moving the separating tool in a reciprocating motion, transverse to the optical axis of the live cornea, to separate additional sections of the other portions of the front and adjacent layers of the live cornea from each other to form a further portion of the pocket between the front and adjacent layers which is defined by additional new edges of the other portions of the front and adjacent layers which remain connected.

21. A method as claimed in claim 18, further comprising the step of further separating sections of the other portions of the front and adjacent layers from each other to form the front layer as a flap which remains pivotably attached to the adjacent layer at a connection portion thereof.

22. A method as claimed in claim 18, wherein the stabilizing step comprises the step of applying suction to the front surface of the live cornea to stabilize the live cornea.

23. A method for separating a front layer of a patient's live cornea from a remainder of the live cornea, comprising the steps of stabilizing the live cornea to substantially restrict the live cornea from moving;

inserting a separating tool into the live cornea at a first depth to separate a portion of the front layer of the live cornea from a portion of an adjacent layer of the live cornea to form a space between the front and adjacent layers defined by edges of other portions of the front and adjacent layers which remain attached to each other, the space having a length extending between two of the edges in a direction transverse to an optical axis of the live cornea;

moving the separating tool from the first depth to a second depth in the live cornea;

while the separating tool is at the second depth, moving the separating tool in a reciprocating motion, transverse to the optical axis of the live cornea to separate sections of the other portions of the front and adjacent layers of the live cornea from each other to form a socket between the front and adjacent layers which is defined by new edges of the other portions of the front and adjacent layers which remain connected, such that the pocket has a length extending between two of the new edges in a direction transverse to the optical axis of the live cornea, the length of the pocket being greater than the length of the space;

moving the separating tool from the second depth to a third depth in the live cornea; and while the separating tool is at the third depth, moving the separating tool in a reciprocating motion, transverse to the optical axis of the live cornea, to separate additional sections of the other portions of the front and adjacent layers of the live cornea from each other to form a further portion of the pocket between the front and adjacent layers which is defined by additional new edges of the other portions of the front and adjacent layers which remain connected;

wherein the step of moving the separating tool in a reciprocating motion at the third depth comprises the step of restricting movement of the separating tool such that the further portion of the pocket has a length extending between two of the additional new edges in a direction transverse to the optical axis of the live cornea, the length of the further portion of the pocket being less than the length of the pocket.

24. A method for forming a substantially circularly shaped pocket between layers of a patient's live cornea, comprising the step of substantially stabilizing the live cornea; and moving a separating tool in a reciprocating motion transverse to the optical axis of the cornea, while automatically restricting the reciprocating motion by different amounts at different depths in the live cornea, to form the substantially circularly shaped pocket between layers of the live cornea.

25. A method as claimed in claim 24, wherein the separating tool has a substantially circularly shaped blade, and the moving step comprises the steps of:

positioning the blade at a depth in the cornea; and moving the blade in the reciprocating motion to form the substantially circularly shaped pocket.

26. A method as claimed in claim 24, further comprising the steps of:

restricting the reciprocating movement of the blade to cause the blade to form the pocket-between the layers of the live cornea; and unrestricting the reciprocating movement of the blade to enable the blade to expand the pocket to form a flap-like layer at the front of the live cornea.

27. A method as claimed in claim 24, wherein the stabilizing step further comprises the step of applying suction to the front surface of the live cornea to stabilize the live cornea.

* * * * *